(12) United States Patent  
Smits

(10) Patent No.: US 6,540,709 B1  
(45) Date of Patent: Apr. 1, 2003

(54) KNEE BRACE WITH SAGITTAL ADJUSTMENT

(75) Inventor: Jan F. A. Smits, Helmond (NL)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 09/762,868

(22) PCT Filed: Sep. 24, 1999

(86) PCT No.: PCT/SE99/01680

§ 371 (c)(1),  
(2), (4) Date: Feb. 14, 2001

(87) PCT Pub. No.: WO00/18337

PCT Pub. Date: Apr. 6, 2000

(30) Foreign Application Priority Data

Sep. 25, 1998 (SE) .............................................. 9803257

(51) Int. Cl.⁷ ................................................. A61F 5/00
(52) U.S. Cl. ........................................... 602/16; 602/26
(58) Field of Search ....................... 602/16, 26; 128/882

(56) References Cited

U.S. PATENT DOCUMENTS

| 4,768,500 A | * | 9/1988 | Mason et al. ................. 602/26 |
| 4,803,975 A | | 2/1989 | Meyers |
| 5,277,698 A | | 1/1994 | Taylor |
| 5,286,250 A | * | 2/1994 | Meyers et al. ................. 602/16 |
| 5,302,169 A | * | 4/1994 | Taylor ......................... 602/16 |
| 5,433,699 A | * | 7/1995 | Smith, III .................... 602/23 |
| 4,565,190 A | | 1/1996 | Pirmantgen et al. |
| 5,485,565 A | | 1/1996 | Tillinghast, III et al. |
| 5,658,243 A | * | 8/1997 | Miller et al. .................. 602/16 |
| 6,027,466 A | * | 2/2000 | Diefenbacher et al. ........ 602/16 |
| 6,039,709 A | * | 3/2000 | Bzoch ......................... 602/16 |
| 6,309,368 B1 | * | 10/2001 | Herzberg et al. ............. 602/16 |

* cited by examiner

Primary Examiner—Michael A. Brown  
Assistant Examiner—Fenn C. Mathew  
(74) Attorney, Agent, or Firm—Ladas & Parry

(57) ABSTRACT

The invention relates to a knee brace with sagittal adjustment, that is a brace or an orthotic device capable of correcting the knee joint into varus or valgus for osteoarthritis treatment. The knee brace comprises a thigh cuff (1) and a shin cuff (2) interconnected by a hinge portion (3) on the lateral side of the knee brace only. According to the invention, the hinge portion is capable of providing a sagittal correction force to correct the position of a knee joint into varus or valgus. Preferably, the hinge portion comprises a structure which may be locked in a curved or angled position to provide the sagittal correction force.

9 Claims, 2 Drawing Sheets

KNEE BRACE WITH SAGITTAL ADJUSTMENT

BACKGROUND OF THE INVENTION

The present invention relates to a knee brace with sagittal adjustment, that is a brace or an orthotic device capable of correcting the knee joint into varus or valgus for osteoarthritis treatment. The knee brace of the invention features a special hinge portion providing a correction force to the thigh cuff and shin cuff attached to the leg of a patient in order to correct the position of the patient's knee joint, especially during extension of the leg.

STATE OF THE ART

The knee joins the femur to the tibia and is controlled by ligaments and cartilage. Contact between the femur and the tibia occurs across the cartilage and there are so called compartments or spaces at each side of the knee. The medial compartment is on the inside of the knee, the lateral compartment is on the outside of the knee.

A healthy knee joint has an even distribution of pressure medially and laterially.

Unicompartmental osteoarthritis, which may occur in the medial compartment or in the lateral compartment, will result in a mechanical malfunction of the knee whereby uneven distribution of pressure occurs across the knee causing excessive wear on the inside of the knee joint in medial compartment osteoarthritis and on the outside of the knee joint in laterial osteoarthritis.

Unicompartmental osteoarthritis can be induced by injury or by aging. With the advancement of the disease, the space between the femur and tibia decreases. The problem may progress to the extent that the space is eliminated and the femur contacts the tibia. In those circumstances, erosion of the tibia may result.

With the disease there is a change in the normal angle between the femur and tibia. Lateral thrust upon heel strike often accompanies the increase in the misalignment of the femur and the tibia. This tends to stretch the ligaments on the opposite side as well as having an adverse effect on the knee joint, tending to emphasize the erosion of the tibia.

A further complication is that rotational slackness develops as the space between the compartment is reduced. This is caused by slackening of the ligaments as the attachment points of the ligaments move closer together with bone deterioration.

Various orthotic devices for knee joints are known. One type of knee brace includes double-sided positive hinge connections, that is lateral and medial hinge mechanisms, to provide a more or less natural motion of the knee joint as well as providing the desired support for relieving pain and as a walking aid etc. However, because of the lateral end medial hinge mechanisms, it is impossible to adjust such orthotic devices in a frontal plane into varus or valgus.

Another type of orthotic devices is the one-sided knee joint, that is having a hinge mechanism on one side only, an example of which may be seen from U.S. Pat. No. 5,277,698. In this knee brace a sagittal adjustment is possible through use of the hinge elements comprising circular hinge elements. The knee brace is capable of applying a force to the knee by means of a cross-strap tightenable across the knee. The knee brace also includes a multiaxial hinge mechanism.

Another example of the one-sided knee joint may be seen from U.S. Pat. No. 5,458,565. In this knee brace a restoring force is achieved through use of a rotary hinge assembly together with an inflatable and deflatable fluid-containing pad positioned between the hinge assembly and the knee joint. The restoring force is adjustable by selective inflation and deflation of the pad. The knee brace also includes a multiaxial geared hinge mechanism.

A problem with this type of knee brace is that the multiaxial hinge mechanism does not provide the best possible natural movement of the knee joint. Also, the cross-strap as well as the fluid-containing pad are bulky and difficult to adjust to an accurate correction force.

The present invention uses another approach to providing the correction force, thus avoiding the above-mentioned problems. In the present invention, the hinge mechanism is adjustable to provide the correction force on the thigh and shin cuffs. Also, the knee brace comprises a four-axes joint providing a more natural movement simulating the movement of the knee.

SUMMARY OF THE INVENTION

The present invention provides a knee brace with sagittal adjustment comprising a thigh cuff and a shin cuff interconnected by a hinge portion on one side of the knee brace only.

According to the invention, the hinge portion is capable of providing a sagittal correction force to correct the position of a knee joint into varus or valgus. Preferably, the hinge portion comprises a tilting mechanism which may be locked in an angled state to provide the sagittal correction force.

The invention is defined in the accompanying claim 1 while preferred embodiments are set forth in the dependent claims.

BRIEF DESCRIPTION OF THE DRAWINGS

The invention will be described in detail below with reference to the accompanying drawings in which.

DETAILED DESCRIPTION OF PREFERRED EMBODIMENTS

Prefabricated knee orthoses in general are designed to stabilise frontal axis movements. Because of the nature of these designs they can control flexion and extension up to a certain extent. If for any reason correction of knee alignment in the frontal plane is required, a custom brace or a brace with a total different design is needed. If besides flexion, adjustments by the sagittal axis are needed to unload the medial or lateral compartment, joints and frame need different functions. Changing the uprights to accommodate for valgus or varus, the use of a second joint becomes difficult, because of the lengthening and shortening of the uprights. Besides these practical reasons, a unilateral joint can be aligned far more easier and the appearance could also benefit. Since these types of braces are mainly used to support the treatment of osteoarthritis and therefore used to minimise pain and to protect the knee joint, the movement of the joint should follow the natural movement as close as possible in order to prevent unnecessary friction between the articulating joint surfaces. The function for the thigh and shin cuffs is to divide pressure and to maintain the proper position on the extremity. Due to the biomechanical nature of the knee joint it is only possible to change alignment of the knee from 30° flexion until full extension. Fortunately also the unloading is wanted in that range of motion. Even if we realize that the use of osteoarthritis valgus or varus knee braces is not yet scientifically proven; in a great number of cases we actually can minimise the pain and maintain mobility of the knee joint for a longer period of time.

The knee brace of the invention consists of a knee joint, a thigh cuff and a shin cuff.

During extension the knee brace is able to correct the position of the knee into valgus or varus. It is biomechanically impossible to keep the knee in the adjusted position during full flexion. For pain relief or to take away the load from the medial or lateral compartment of the knee this is also not needed. From approx. 30° of flexion to full extension the brace will correct the adjusted valgus or varus position.

The knee of an osteoarthritis patient is sensitive to all kind of friction or forces; so non-physiological movement must be prevented. For this reason a knee joint with a "natural movement" was designed. This so-called four-axes knee joint begins flexion with an anterior movement followed by rotation in a C-shaped joint motion path. In full extension the rotation axis is located 15 cm above the tibial plateau and dorsally of the joint. The anterior translation of the proximal upright is 11 mm. The joint comprises a tilting mechanism which allows for sagittal adjustments as is described more in detail below. Although the joint is not designed to prevent hyperextension, an extension stop is present (not shown).

Figure 1:
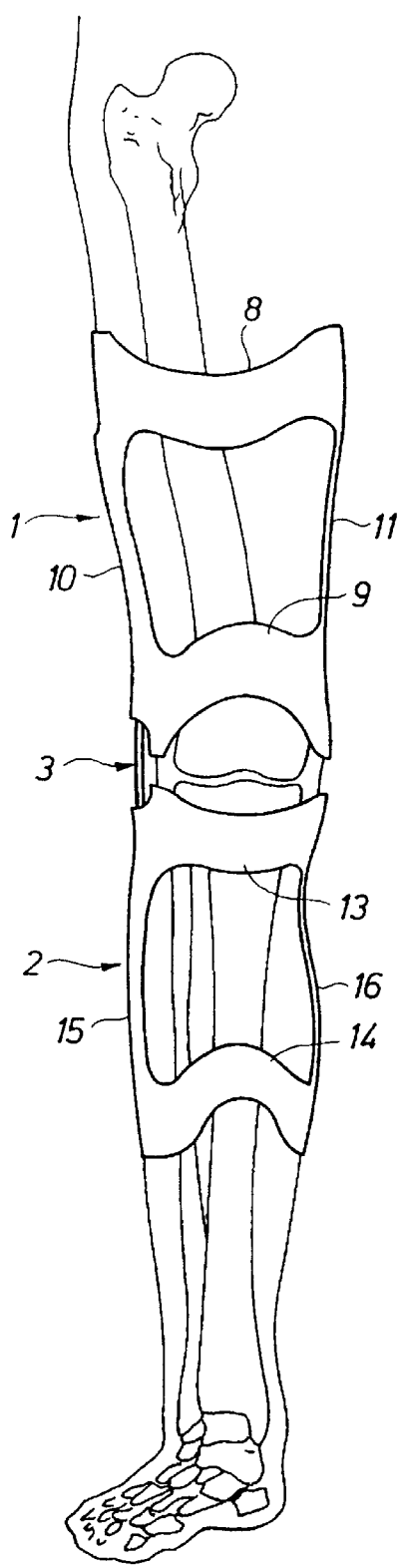
FIG. 1 is a front view of a knee brace in accordance with the invention attached to the right leg of a patient.
Figure 2:
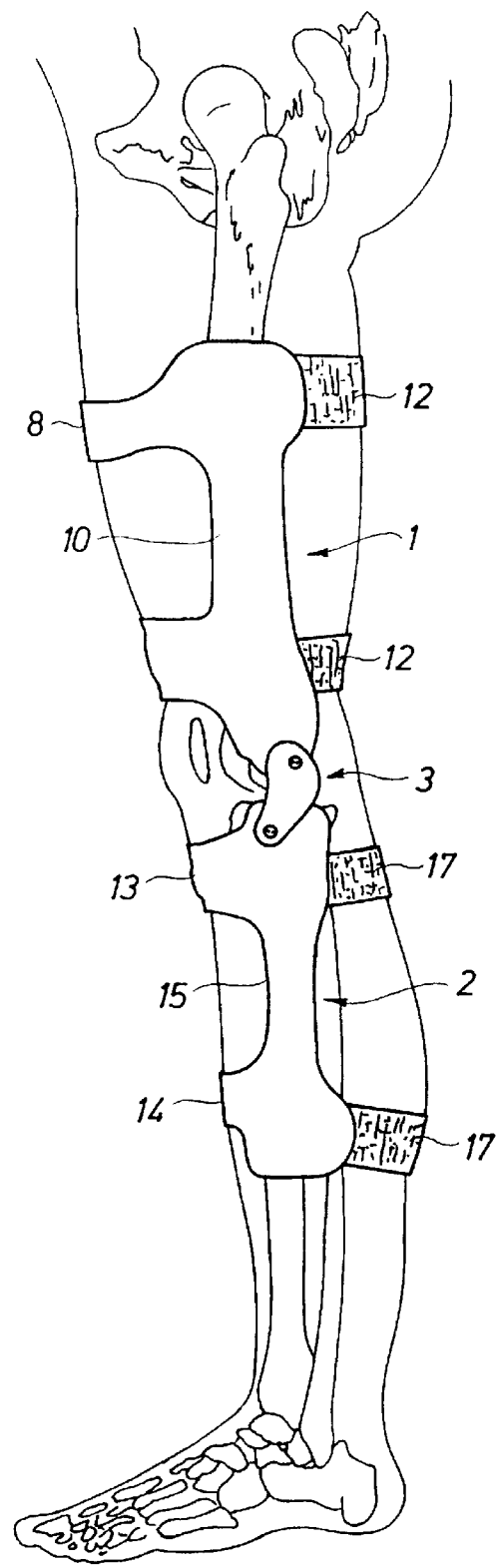
FIG. 2 is a side view of a knee brace of the present invention attached to the left leg of a patient.

In FIGS. 1 and 2, the knee brace is shown attached to the leg (right and left, respectively) of a patient. The thigh cuff 1, constructed out of composite is designed to achieve a grip on the femur bone by surrounding the soft tissue. The distal end reaches until the condyles for stabilizing the knee joint. The thigh cuff 1 has rigid areas to achieve proper function; a lateral strut 10 and a proximal 8 and distal 9 thigh band. The medial vertical strut 11 is integral with the distal horizontal band 9 and the proximal thigh band 8. The horizontal bands 8, 9 are rigid at the lateral sides, providing a rigid connection to the lateral strut 10, while the medial sides are thinner and more flexible for size adjustability and for comfort. The thigh cuff 1 is closed with adjustable dorsal bindings 12.

The shin cuff 2, constructed out of composite, is designed to achieve a grip on the tibia and the fibula bone by surrounding the soft tissue. The proximal end reaches until the condyles for stabilizing the knee joint. The shin cuff 2 has rigid areas to achieve proper function; a lateral strut 15 and a proximal 13 and distal 14 shin band. The medial vertical strut 16 is integral with the proximal horizontal band 13 and the distal shin band 14. The horizontal bands 13, 14 are rigid at the lateral sides, providing a rigid connection to the lateral strut 15, while the medial sides are thinner and more flexible for size adjustability and for comfort. The shin cuff 2 is closed with adjustable dorsal bindings 17.

Both the thigh cuff and the shin cuff are replaceable and produced in three different sizes (small, medium, large) in order to fit legs of various sizes. It is possible to combine e.g. a small shin cuff with a medium thigh cuff and all other combinations.

Figure 3:
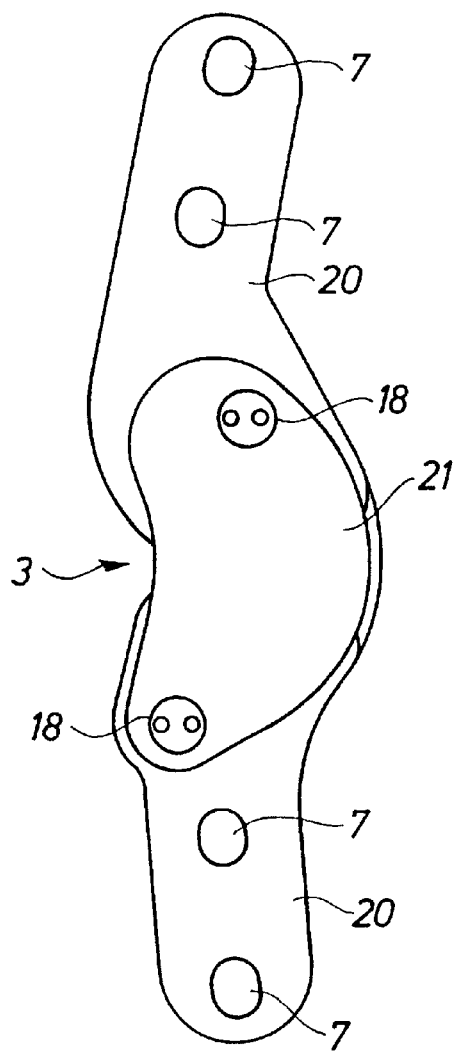
FIG. 3 is a side view of the hinge elements of the present invention.

The hinge elements are shown in FIG. 3 without the cuffs. The hinge is preferably located at the lateral side. The hinge portion consists of uprights 20 for attachment to the thigh and shin cuffs and hinge plates 21. The uprights have holes 7 for attachment to the respective cuff as will be explained more in detail below. The hinge plate 21 is provided with two of the four axes 18 to achieve the desired articulated connection between the uprights. The other two axes 18 are connected by an element (not shown) located inside the hinge plates 21.

Figure 4:
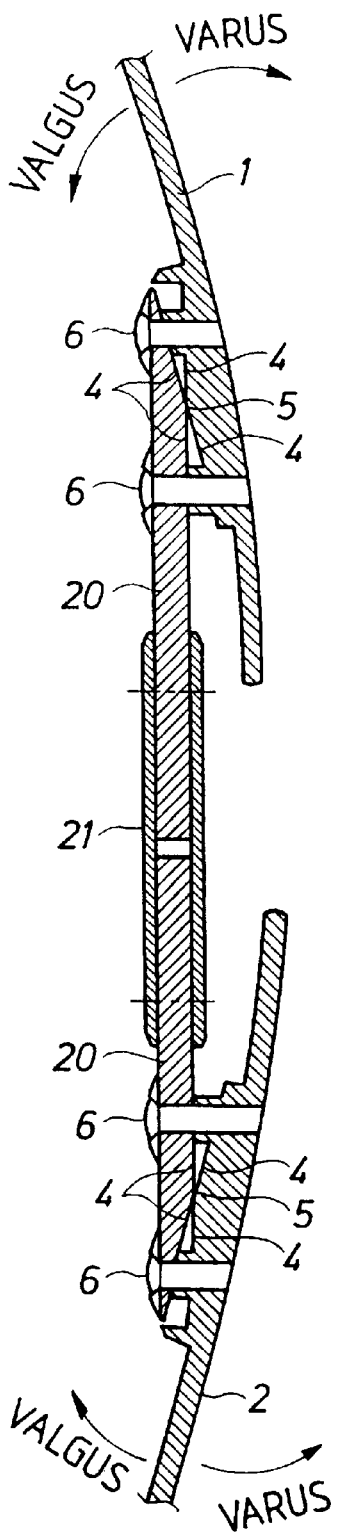
FIG. 4 is a front view in cross-section of the hinge elements.

In FIG. 4 the hinge elements are shown together with parts of the thigh cuff 1 and the shin cuff 2 in cross-section. It will be seen that the uprights 20 are connected to the hinge plates 21 forming the four axes joint. The uprights 20 are attached to the thigh cuff 1 and shin cuff 2 by means of adjustment fixtures. For best possible adjustment, it is suitable that there are two adjustment fixtures, one each for the thigh and shin cuff, respectively. The adjustment fixtures comprise tilting mechanisms 4 and two pairs of screws 6 fitted in the holes 7. The holes 7 are oval to provide a clearance between the holes 7 (FIG. 3) and the screws 6 such that an angle adjustment is possible. The tilting mechanism is formed by opposed V-shaped faces 4 on the cuffs 1, 2 and the uprights 20, respectively, such that the cuffs 1, 2 are in line contact at 5 with the respective upright 20 along a sagittal axis (an axis parallel with the sagittal plane) Thus, the angle between the cuffs and upright elements may be adjusted by tilting around the sagittal axis at the contact line 5. One screw 6 is located at each side of the contact line 5.

The tilting angle is set by adjusting the respective pair of screws 6, that is one screw is tightened while the other screw is loosened or vice versa. In this way, a positive adjustment fixture is obtained. Thus, when the knee brace is attached to the leg of a patient, the angle between the cuffs 1,2 and the uprights 20 of the hinge results in a biasing force which acts as a correction force to provide the desired valgus or varus position.

Thus, it will be appreciated that the knee brace of the present invention provides a sagittal correction force, which is caused by the hinge portion without any use of a cross-strap or inflatable pad. The force or angle adjustment is easily achieved by setting the pairs of screws. This can be done even when the patient is wearing the knee brace. Also, the thigh cuff and shin cuff are designed as partly rigid cages which hold the knee brace firmly on the patient's leg. The thigh and shin cuffs are interchangeable with various sizes, so that the knee brace is easily adapted for different sizes of the patient's thigh and shin. The scope of the invention is only limited by the claims below.

What is claimed is:

1. A knee brace for use with a knee joint having a sagittal adjustment comprising a thigh cuff and a shin cuff interconnected by a hinge portion only on one side of the knee brace at an adjustable angle, wherein the hinge portion is capable of providing a sagittal correction force to correct a position of the knee joint into varus or valgus by means of a tilting mechanism formed by a cuff element in contact with an upright element, so that the angle between the elements may be adjusted, wherein the tilting mechanism comprises opposed V-shaped faces on the cuffs and the uprights, such that the cuffs are in line contact with the respective upright along a sagittal axis.

2. A knee brace according to claim 1, wherein the adjustment of the angle is set by means of at least one pair of screws, of which one screw is located at each side of the contact.

3. A knee brace according to claim 1, wherein the thigh cuff consists of a cage comprising a proximal band, a distal band, a lateral strut, a medial strut and dorsal bindings.

4. A knee brace according to claim 3, wherein parts of the proximal band, the distal band, and the lateral strut of the thigh cuff are rigid.

5. A knee brace according to claim 1, wherein the shin cuff consists of a cage comprising a proximal band, a distal band, a lateral strut, a medial strut and dorsal bindings.

6. A knee brace according to claim 5, wherein parts of the proximal band, the distal band, and the lateral strut of the shin cuff are rigid.

7. A knee brace according to claim 1, wherein the thigh cuff and/or the shin cuff are interchangeable with various sizes.

8. A knee brace according to claim 1, wherein the hinge portion comprises a four axes joint.

9. A knee brace according to claim 8, wherein the motion of the joint follows a C-shaped path in which, at full extension, the rotation axis of the joint is located approximately 15 cm above the tibial plateau and dorsally of the joint and, at the beginning of the motion, the anterior translation of the proximal upright is approximately 11 mm.

* * * * *